United States Patent
Jabri et al.

(10) Patent No.: US 8,705,695 B2
(45) Date of Patent: Apr. 22, 2014

(54) REGION OF INTEREST DETERMINATION FOR X-RAY IMAGING

(75) Inventors: Kadri Nizar Jabri, Oak Creek, WI (US); Vivek Walimbe, Pewaukee, WI (US); Rowland Saunders, Hartland, WI (US); Romain Areste, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 655 days.

(21) Appl. No.: 12/953,274

(22) Filed: Nov. 23, 2010

(65) Prior Publication Data

US 2012/0128125 A1    May 24, 2012

(51) Int. Cl.
*G01N 23/04*    (2006.01)

(52) U.S. Cl.
USPC ............................................ 378/62; 378/98.5

(58) Field of Classification Search
USPC ................................. 378/4, 15, 13, 62, 98.5
See application file for complete search history.

(56) References Cited

U.S. PATENT DOCUMENTS

| | | | |
|---|---|---|---|
| 2002/0054662 A1* | 5/2002 | Verdonck et al. | 378/62 |
| 2009/0092224 A1* | 4/2009 | Nishide et al. | 378/13 |
| 2009/0279663 A1* | 11/2009 | Miyamoto | 378/62 |
| 2009/0310741 A1* | 12/2009 | Borghese et al. | 378/37 |

* cited by examiner

*Primary Examiner* — Irakli Kiknadze
(74) *Attorney, Agent, or Firm* — Fletcher Yoder, P.C.

(57) ABSTRACT

A radiography system allow for user determination of a region of interest on a subject prior to X-ray exposure. The region of interest is defined by user interaction with an image, a pointer system, or the like. The region of interest is then translated to the imaging coordinate system, such as in the plane of a digital detector. The region is then used for exposure control during an imaging sequence, either in an open or closed-loop manner.

16 Claims, 3 Drawing Sheets

REGION OF INTEREST DETERMINATION FOR X-RAY IMAGING

BACKGROUND OF THE INVENTION

The present invention relates generally to field of X-ray imaging systems, and more particularly to optimization to radiation dosage by specific definition of a region of interest to be imaged.

Radiography systems, such as X-ray systems, are used to generate images showing internal features of a subject. In the medical context, such systems are used for viewing internal anatomies and tissues, such as for diagnostic purposes. In modern projection X-ray systems, for example, X-rays are generated by an X-ray source and are directed to a patient or other subject. The X-rays transfer through the subject, and are absorbed or attenuated by internal features. The resulting X-rays impact a digital detector where image data is generated. Collecting the image data allows for reconstruction of a useful image. Similar techniques are used for computed tomography, fluoroscopy and tomosynthesis image generation.

It is a general goal in radiography to acquire sufficient image data for reconstruction of a useful image, while optimizing (often minimizing) the dosage of radiation. Various techniques have been developed for estimating or controlling the imaging process to obtain these goals. Current radiography systems using automatic exposure control or photo-timing to control exposure (and consequently dose) to the patient rely on proper alignment of patient anatomy to fixed locations on the system. These locations usually contain means for measuring exposure, such as ionization or ion chambers. Exposures are terminated when a certain exposure level is reached. Problems arise, however, in situations where it is difficult to align body parts with the fixed locations on the system, especially when these fixed locations are not properly adapted to the patient anatomies, patient sizes, and so forth. By way of example, pediatric imaging is especially challenging because it is often difficult to align smaller body parts with the ion chambers of the imaging system. Extremity imaging, both adult and pediatric, faces similar challenges. Because the exposure measurement devices, such as ion chambers serve as integrators of received radiation, misalignment may result in under or over estimating the actual radiation actually applied to the anatomy of interest.

To avoid over-exposure or under-exposure resulting from such misalignment, operators may avoid using photo-timing and automatic exposure control and revert to fixed time exposures. This manual technique is very dependent on operator skill and on the subjective estimation of the exposure needed to realize a clinically useful image and image quality.

Improved techniques are needed in the field that will permit proper exposure timing or exposure control and avoid such drawbacks in the prior art.

BRIEF DESCRIPTION OF THE INVENTION

The present invention provides a novel technique designed to respond to such needs. The technique is based upon the identification of a region of interest of the subject that is a subset of the overall field of view current in the X-ray imaging system. The region of interest may be defined in various manners, such as through the use of wired or wireless devices in the field of view, the use of patient or system images with which an operator may interact to define the region of interest, and so forth. The region of interest, once defined, is then translated into the imaging system coordinates, such as by reference to regions of a digital detector anticipated to fall within the desired region of interest. Parameter settings of the X-ray exposure, then, may be calculated, along with exposure settings, to perform open-loop imaging based upon this region of interest definition. Closed-loop control may also, or alternatively be performed based upon similarly defining the region of interest. The technique may be used with or without specialized sensors that provide an indication of integrated exposure levels.

In accordance with one aspect of the invention, a method of X-ray imaging is provided that includes identifying a region of interest with respect to a subject positioned in an X-ray imaging system, the region of interest being a subarea of a field of view of the X-ray imaging system. The region of interest is translated into coordinates of the X-ray imaging system, and X-ray exposure is controlled during an imaging sequence of the X-ray imaging system with the subject based upon the transformed coordinates.

The invention also provides a method for X-ray imaging that begins with positioning a subject in an X-ray imaging system, and identifying a region of interest with respect to the subject positioned in an X-ray imaging system, the region of interest being a subarea of a field of view of the X-ray imaging system. The X-ray exposure is then controlled during an imaging sequence of the X-ray imaging system with the subject based upon the region of interest, and a signal representative of an integral of exposure for the region of interest is monitored during the exposure.

The invention also provides a system for X-ray imaging that comprises means for identifying a region of interest with respect to a subject positioned in an X-ray imaging system, the region of interest being a subarea of a field of view of the X-ray imaging system. A processing circuit is configured to transform the region of interest into coordinates of the X-ray imaging system. A system controller is configured to control X-ray exposure during an imaging sequence of the X-ray imaging system with the subject based upon the transformed coordinates.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
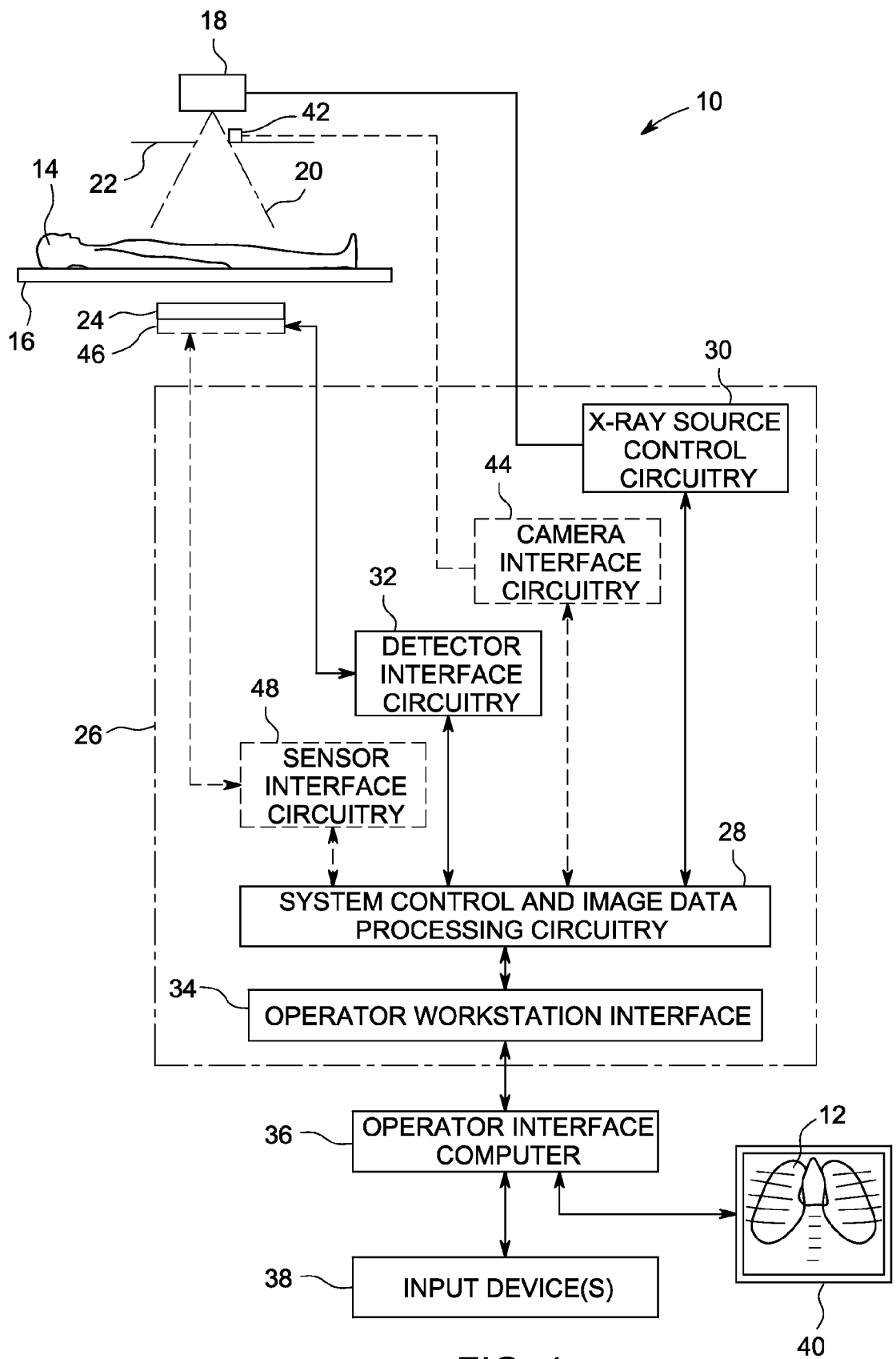
FIG. 1 is a diagrammatical representation of an X-ray imaging system designed to permit specification of a region of interest and translation of the region of interest into the system coordinates for X-ray exposure control.

Referring to FIG. 1, an X-ray imaging system 10 is illustrated that allows for identification of a region of interest and exposure control based upon the region of interest. The X-ray imaging system 10 is adapted for generating images 12 of a subject 14. In a medical diagnostic context, the subject 14 may be positioned on a support 16. An X-ray source 18 is adapted to produce a beam of radiation 20 which passes through collimator 22. The radiation traverses the subject, with some of the radiation being attenuated or absorbed, and resulting radiation impacting a detector 24.

A control and processing system 26 is coupled to both the radiation source and the detector 24. In general, this system allows for regulation of operation of both the source and the detector, and permits collection of information from the detector for reconstruction of useful images. In the illustrated embodiment, for example, the control and processing system 26 includes system control and image processing circuitry 28. Such circuitry will typically include a programmed processor, supporting memory, specific applications executed by the processor during operation, and so forth. The circuitry 28 will be coupled to X-ray source control circuitry 30 that itself allows for control of operation of the X-ray source 18. The X-ray source control circuitry 30 may, for example, under the direction of the system control and image data processing circuitry 28, regulate the current and voltage applied to the X-ray source, trigger the generation of X-rays from the source, trigger startup and shutdown sequences of the source, and so forth.

The system control and image data processing circuitry 28 is further coupled to detector interface circuitry 32. This circuitry allows for enabling the digital detector, and for collecting data from the digital detector. As will be appreciated by those skilled in the art, various designs and operations of such detectors and detector interface circuitry are known and are presently in use. Such designs will typically include detectors having an array of discrete pixel elements defined by solid state switches and photodiodes. The impacting radiation affects the charge of the photodiodes, and the switches allow for collection of information regarding the impacting radiation (e.g., depletion of charge of the photodiodes). The information may then be processed to develop detailed images in which gray levels or other features of individual pixels in an image are indicative of the radiation impacting corresponding regions of the detector.

The control and processing system 26 is also illustrated as including an operator workstation interface 34. This interface allows for interaction by an operator who will typically provide inputs through an operator interface computer 36. The operator interface computer 36 and/or the system control and image data processing circuitry 28 may perform filtering functions, control functions, image reconstruction functions, and so forth. One or more input devices 38 are coupled to the operator interface computer 36, such as keyboards, computer mice, and so forth. The operator interface computer 36 is further coupled to a monitor 40 on which images may be displayed, instructions may be provided, regions of interest may be defined as discussed below, and so forth. In general, the operator interface computer 36 may include memory and programs sufficient for displaying the desired images, and for performing certain manipulative functions, in particular the definition of a region of interest for image exposure control.

It should be noted that, while through the present discussion reference is made to an X-ray system in the medical diagnostic context, the present invention is not so limited. For example, the invention may be used for other radiological applications, such as fluoroscopy, computed tomography, tomosynthesis and so froth. The system may be used in other application contexts as well, such as part and parcel inspection, screening and so forth. Moreover, in certain contexts, and certain aspects of the invention may be used with non-digital detectors, such as conventional film.

The system illustrated in FIG. 1 is adapted to allow for selection or definition of a region of interest that will serve for exposure control during imaging sequences. In the particular embodiment illustrated, a camera 42 may be positioned above the patient and coupled to camera interface circuitry 44. It is contemplated that the camera may be used to generate images of the subject that can form the basis for operator definition of a region of interest as described below. The camera interface circuitry would allow for triggering the camera to collect an image or images that can be processed by the camera interface circuitry and forwarded to the system control and image data processing circuitry 28. The image may then be conveyed to the operator interface computer 36 and displayed on the monitor 40. In accordance with another aspect of the system illustrated in FIG. 1, one or more sensors may be provided as indicated by reference numeral 46 in FIG. 1. Where provided, such sensors may be interfaced with sensor interface circuitry 48 which, in turn, communicates with the system control and image data processing circuitry 28. As discussed below, such sensors may allow for detection of exposure in specific regions of the imaging system based upon the definition of the region of interest. Sensors 46 may include, for example, sensors provided on the back of a detector, segmented ion chambers, and so forth. Sensors of this type are described, for example in U.S. patent application Ser. No. 11/426,009, entitled Wireless Integrated Automatic Exposure Control Module, filed on Jun. 22, 2006 in the name of Saunders, which is hereby incorporated into the present disclosure by reference.

Figure 2:
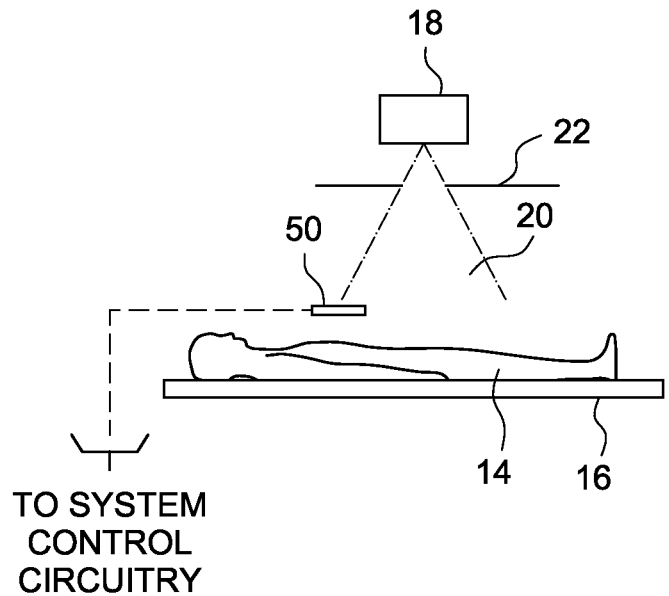
FIG. 2 is diagrammatical illustration of a portion of a system of the type shown in FIG. 1, utilizing a pointing device to indicate a region of interest.

FIG. 2 illustrates an alternative configuration in which a pointing device 50 is used to define a region of interest. As will be appreciated by those skilled in the art, various forms of such devices are known and may be used in the present environment. For example, magnetic field and radiofrequency pointing devices have been developed that allow for detection of position of the pointing device in a known volume. Devices of this type are described, for example, in U.S. patent application Ser. No. 11/702,355, entitled Electromagnetic Tracking Method and System, filed on Feb. 5, 2007 in the name of Anderson, which is hereby incorporated into the present disclosure by reference.

Figure 3:
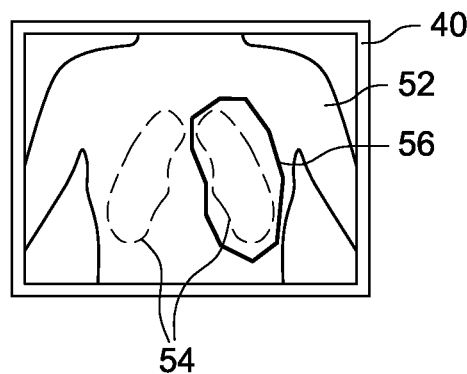
FIG. 3 is a simplified exemplary image of a subject with a region of interest defined by an operator.

FIG. 3 illustrates an image of a subject in which a region of interest is defined. The image 52 is illustrated as being displayed on a monitor 40. The image may or may not show actual internal anatomies or structures of the subject, although, by way of example, the lungs 54 of a human patient are illustrated in the figure. Depending upon the technique used to define the region of interest, the image may indicate the region of interest in various manners. For example, at least three techniques are presently contemplated for establishing the region of interest. Firstly, a photographic-type image could be made via a camera of the type illustrated in FIG. 1. This image may then be displayed on a monitor and any suitable pointing device may be used to outline a region of interest, such as a computer mouse, a digitizer, a touch screen, and so forth. The region of interest may be designated in any suitable manner, such as indicated by the heavy outline 56 in FIG. 3. In another presently contemplated approach, an X-ray pre-shot at low dosage may be made via the X-ray system and the resulting image reconstructed and displayed for the operator. This somewhat low quality image may be used to identify the region of interest in a similar manner. Moreover, various navigational tools and pointing devices may be used as generally illustrated in FIG. 2 and discussed above. Where such devices are employed, the region of interest may be outlined in a similar manner for verification or modification by the operator.

Figure 4:
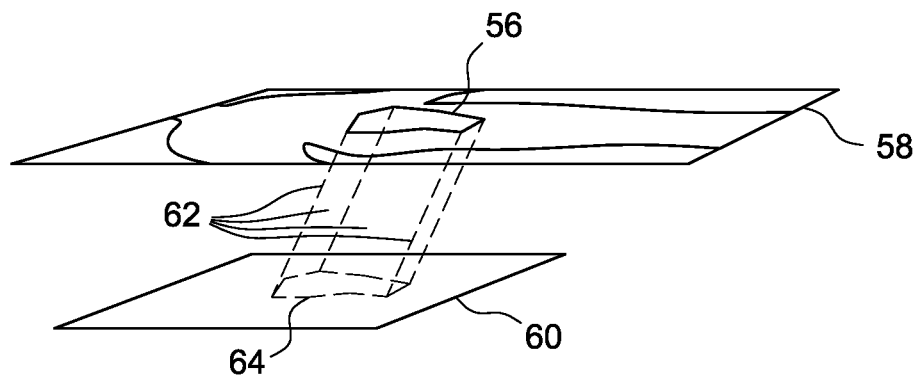
FIG. 4 is a diagrammatical representation of a translation of a region of interest defined by an operator to imaging system coordinates.

Once the particular region of interest is outlined, a transformation may be performed between the region of interest in the plane or space in which it is made by the operator and the coordinate system of the imaging system. In certain presently contemplated embodiments, for example, the region of interest is projected into the plane of a digital detector as illustrated in FIG. 4. The region of interest 56 is illustrated as displayed in a first reference plane 58 which may be a plane of an image generated of the subject, and projected into a second or system reference plane 60. Depending upon the location and orientation of the X-ray source, the location and orientation of the subject, and the location and orientation of the detector, then, translational calculations may be made that project the region of interest, as indicated by reference numeral 62 in FIG. 4 to a corresponding region 60 in the coordinate system of the imaging system, as indicated by the detector plane 60 in FIG. 4. It is contemplated that the position and orientation of the source can be known by conventional techniques, as can the position orientation of the detector. Thus, the computations for translation of the region of interest 56 to the system coordinate system are straightforward and well within the ambit of one skilled in the art.

Figure 5:
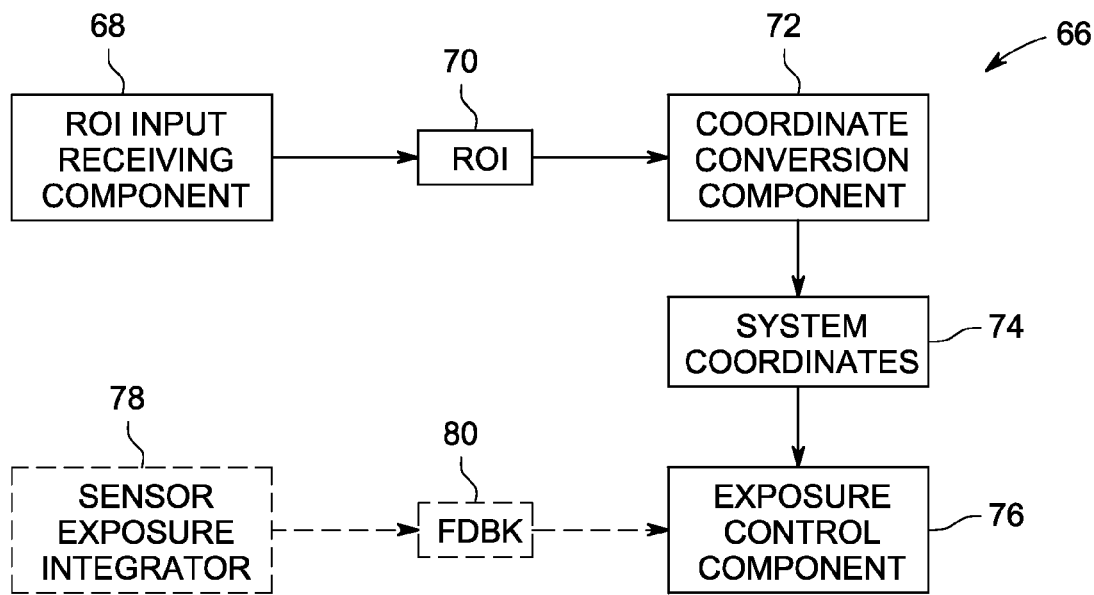
FIG. 5 is a diagrammatical illustration of certain functional components that may be used for the region of interest definition, translation, and exposure control.

FIG. 5 illustrates exemplary components of the system of FIG. 1 may be used for determining the region of interest and for subsequently controlling exposure during an X-ray examination sequence. The subsystem, designated generally by reference numeral 66 in FIG. 5, includes a region of interest input receiving component 68 that produces a region of interest 70. As noted above, the input receiving component 68 may include, for example, one or more components of a workstation at which an operator selects or outlines a region around a desired anatomy or portion of a subject. The input receiving component may also include elements of a pointing system that allow for a designation of region of interest in the space between the X-ray source and the subject. The resulting region of interest 70 is an outline of the particular region that should be used as a basis for exposure control. A coordinate conversion component 72 accepts the region of interest 70 and converts the region of interest coordinates into the imaging system coordinates 74. As noted above, this coordinate conversion component may simply translate the region of interest coordinates into a particular plane of the imaging system, such as the detector plane. In certain embodiments, this conversion may be simplified, such as where a region of interest is identified on an X-ray image pre-shot that is effectively made in the plane of the detector. An exposure control component, then, serves to control parameters of the X-ray system for a subsequent exposure in which the region of interest, or more particularly the system coordinate system translate a region of interest, is used to control such operational parameters as the current and duration, and voltage applied to the X-ray source, commonly referred to as the mAs and the kV. Various techniques may used to control this exposure in an open-loop manner, such as the use of a pre-shot. Moreover, closed-loop control of the exposure may also be performed, such as via the use of sensors or exposure integrators as indicated by box 78 in FIG. 5. When used, such sensors or integrators will provide feedback 80 to the exposure control component 76 such that the exposure can be controlled to reach a desired integrated level of dosage. It should be noted that the components designated by reference numerals 72 and 76 will typically be defined by firmware or software in the control and processing system 26 illustrated in FIG. 1. While these components could be formed separately, they essentially will build upon existing X-ray system control techniques well-known in the art.

Figure 6:
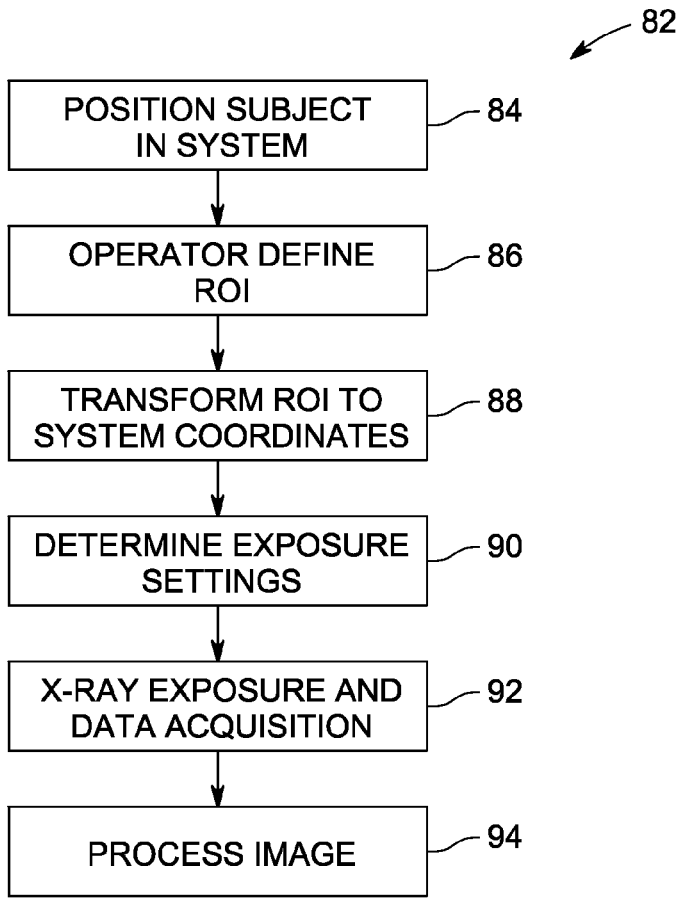
FIG. 6 is a flow chart illustrating exemplary logic for performing region of interest definition, translation, and subsequent exposure control.

FIG. 6 is a flow chart illustrating exemplary logic for carrying out the exposure control described above based upon a designated region of interest. The logic, designated generally by reference numeral 82, begins with positioning a subject in the imaging system as indicated by reference numeral 84. As in conventional systems, the subject may be positioned for exposure of a particular anatomy of interest, depending upon the purpose of the examination. Step 84 may also include appropriately positioning a detector opposite a source, and positioning the source, orienting the source, defining the field of view, and so forth. At step 86, then, the operator defines a region of interest on the subject. Again, this can be performed by reference to various types of images displayed on computer interfaces, via various pointing devices and locating systems and so forth. Once the region of interest has been defined, then, when necessary the region of interest is transformed to the system coordinates as indicated by block 88 in FIG. 6. Based upon the system coordinates for the region of interest, then, exposure settings are determined as indicated by reference numeral 90. Again, such settings will typically include those settings for the X-ray source, such as the current, voltage, duration of exposure, and so forth. As indicated at step 92, then, the X-ray exposure is performed, either in an open-loop or closed-loop manner, and the X-ray data is acquired. Finally, at step 94 the X-ray data is stored and image may be processed immediately or subsequently based upon the collected X-ray image data. It should be noted that, in many applications, this step may include displaying the region of interest back to an operator relative to a resulting X-ray image. This may be done by superimposing the defined region of interest on the reconstructed image, and where desired, allowing an operator to remove the superimposed region of interest definition from view when not needed. Such display may aid the operator in confirming that he/she has selected the correct region of interest relative to the anatomies or tissues of interest.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of X-ray imaging, comprising:
identifying a region of interest with respect to a subject positioned in an X-ray imaging system, wherein the region of interest is identified via a pointing device manipulated by an operator with respect to the X-ray imaging system, the region of interest being a subarea of a field of view of the X-ray imaging system;
transforming the region of interest into coordinates of the X-ray imaging system;
controlling X-ray exposure during an imaging sequence of the X-ray imaging system with the subject based upon the transformed coordinates; and
displaying the region of interest to an operator relative to the acquired X-ray image.

2. The method of claim 1, comprising generating an image of the subject, and wherein the region of interest is identified by reference to the image.

3. The method of claim 2, wherein the image comprises an X-ray pre-shot image.

4. The method of claim 2, wherein the image comprises a camera image of the subject.

5. The method of claim 2, comprising displaying the image on a monitor, and wherein identifying the region of interest comprises identifying a location of the region of interest on the displayed image.

6. The method of claim 1, wherein transforming the region of interest into coordinates of the X-ray imaging system comprises determining a region of a digital X-ray detector corresponding to the region of interest.

7. The method of claim 1, wherein controlling X-ray exposure based upon the transformed coordinates comprises controlling at least milli-ampere-seconds (mAs) and kilovolts (kV) for the exposure.

8. The method of claim 1, wherein the X-ray exposure is controlled in an open-loop manner.

9. The method of claim 1, wherein the X-ray exposure is controlled in a closed-loop manner.

10. The method of claim 9, wherein the X-ray exposure is controlled based upon feedback from one or more sensors disposed adjacent to a digital X-ray detector.

11. A method of X-ray imaging, comprising:
positioning a subject in an X-ray imaging system;
generating an image of the subject;
identifying a region of interest with respect to the subject positioned in an X-ray imaging system, wherein the region of interest is identified by reference to the image, the region of interest being a subarea of a field of view of the X-ray imaging system;
controlling X-ray exposure during an imaging sequence of the X-ray imaging system with the subject based upon the region of interest; and
monitoring a signal representative of an integral of exposure for the region of interest during the exposure.

12. The method of claim 11, comprising transforming the region of interest into coordinates of the X-ray imaging system, and wherein controlling the X-ray exposure based upon the region of interest comprises controlling the X-ray exposure by reference to the transformed coordinates.

13. The method of claim 11, comprising using the signal representative of the integral of exposure for closed-loop control of the X-ray exposure.

14. The method of claim 11, wherein the signal representative of the integral of exposure is generated by one or more sensors adjacent to a digital X-ray detector.

15. The method of claim 11, wherein the signal representative of the integral of exposure is generated by a digital X-ray detector.

16. A system for X-ray imaging, comprising:
means for identifying a region of interest with respect to a subject positioned in an X-ray imaging system, wherein the means for identifying the region of interest comprises a camera for making an image of the subject and a workstation configured to receive a user input that identifies the region of interest based upon display of the image, the region of interest being a subarea of a field of view of the X-ray imaging system;
a processing circuit configured to transform the region of interest into coordinates of the X-ray imaging system; and
a system controller configured to control X-ray exposure during an imaging sequence of the X-ray imaging system with the subject based upon the transformed coordinates.

* * * * *